United States Patent [19]

Mills et al.

[11] Patent Number: 5,111,396

[45] Date of Patent: May 5, 1992

[54] PORTABLE ECG DATA-STORAGE APPARATUS

[75] Inventors: Gary N. Mills, Gladstone; Habib Homayoun, Aloha; Herbert J. Semler, Portland, all of Oreg.

[73] Assignee: Instromedix, Inc., Hillsboro, Oreg.

[21] Appl. No.: 433,756

[22] Filed: Nov. 9, 1989

[51] Int. Cl.$^5$ .................. G06F 15/42; A61N 1/36
[52] U.S. Cl. ..................... 364/413.06; 364/413.05; 128/696; 128/710
[58] Field of Search .............. 364/413.02, 413.03, 364/413.04, 413.05, 413.06; 128/696, 700, 702, 710, 711

[56] References Cited

U.S. PATENT DOCUMENTS

| | | | |
|---|---|---|---|
| 3,934,267 | 1/1976 | Kosaka et al. | 128/711 |
| 4,576,178 | 3/1986 | Johnson | 128/670 |
| 4,622,979 | 11/1986 | Katchis et al. | 128/702 |
| 4,653,022 | 3/1987 | Koro | 364/900 |
| 4,779,199 | 10/1988 | Yoneda et al. | 364/413.03 |
| 4,895,161 | 1/1990 | Cudahy et al. | 128/710 |
| 4,945,477 | 7/1990 | Edwards | 364/413.06 |

Primary Examiner—Jerry Smith
Assistant Examiner—Russell Cass
Attorney, Agent, or Firm—Kolisch, Hartwell, Dickinson, McCormack & Heuser

[57] ABSTRACT

Portable, two-way ECG data-storage apparatus for the selective window-capturing of successive plural-lead ECG data records. The apparatus receives its information from the analogue output terminals in a conventional ECG machine, and operates a store multiple-lead data in flagged time-windowed fashion in order to assure stable signal information and efficient meory use. Playback can occur either directly in an analogue manner back to any selected ECG machine, and/or audibly for listening to by a user or for transtelephonic transmission.

5 Claims, 1 Drawing Sheet

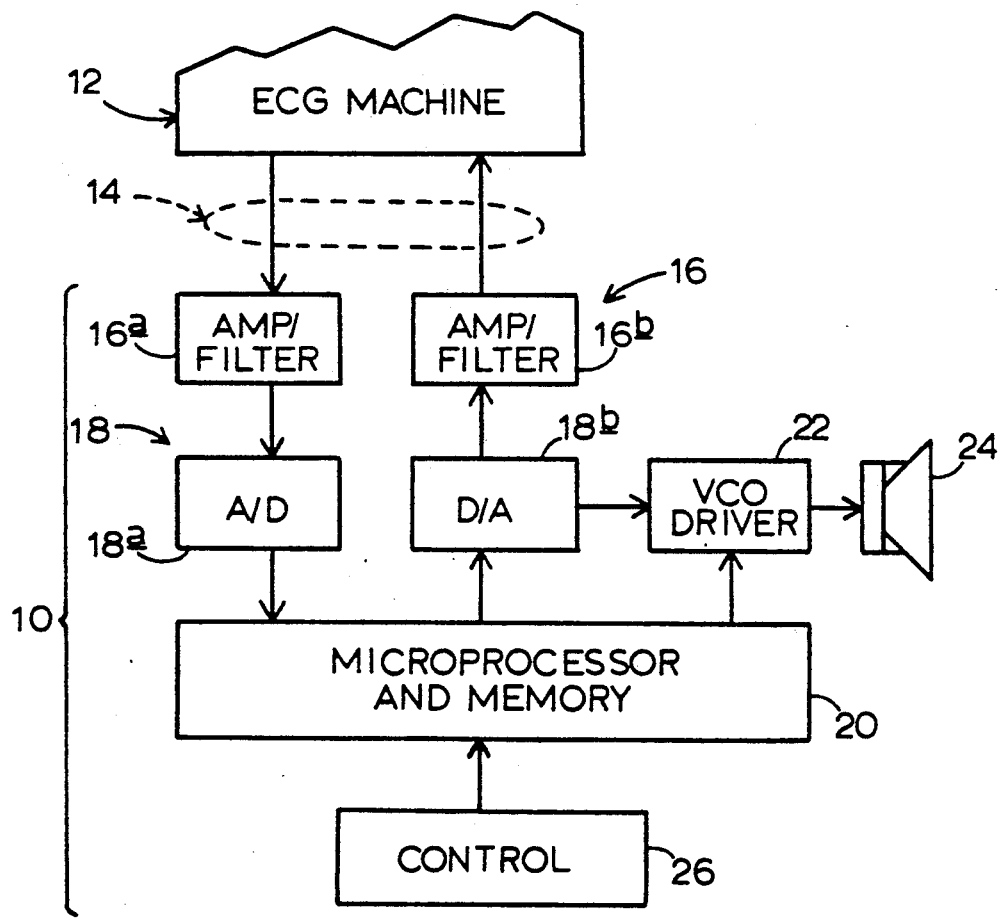

PORTABLE ECG DATA-STORAGE APPARATUS

BACKGROUND AND SUMMARY OF THE INVENTION

This invention relates to portable ECG data-storage apparatus, and more particularly to such which is capable of recording, transporting, and playing back, conveniently, multiple-lead ECG data.

In the field of cardiology, wherein many devices in recent years have been introduced to improve the acquiring, handling, and analysis of ECG data, there remains a need for the availability of a compact, portable ECG data-recording device which is capable of recording multiple-lead analogue signals made available by a conventional ECG machine for later playback, broadcast (via telephonic transmission, etc.), and analysis at some other location.

Hand-held ECG recorders which are now available that, themselves, directly attach to the human body to take in and record an ECG signal, have very limited storage capacity, and are not suitable for acquiring and holding multiple-lead (such as 12-lead) ECG data. Too much time is required in the process of switching from lead to lead, and for allowing signal stabilization to occur, to make easily portable a device having a memory capacity sufficiently large to allow all of this activity.

An important object of the present invention is to address this situation by offering an ECG data-storage device which does not attach directly to the human body, but rather, receives its input signal from the analogue output terminals of a conventional ECG machine which itself is attachable to a patient's body.

The proposed device, under operator control, offers successive, flagged, time windows during which it is capable of recording and storing the analogue EC signals supplied to it from such an external machine. Memory utilization does not occur except during these time windows, and only after an operator signals the device that a new lead is in place, and that signal stabilization (as, for example, is determined by looking at a strip chart) has bee achieved. While different time windows might be selected, one that has been found to be particularly useful is a 5-second time window.

The device is equipped with suitable analogue/digital conversion apparatus, whereby such an analogue signal is converted into digitally recorded data for later playback. Playback can occur, according to the invention, either directly back to an artifact of the originally recorded analogue signal, for recoupling to an ECG machine for strip chart reporting, etc., and/or can be played out audibly for a user to hear, or in a suitably frequency-coded form for transtelephonic transmission to a remote location.

The device proposed by the invention is capable of handling up to a full 12-lead collection of data, with each time-windowed record in memory suitably flagged so that it is readily identifiable later during playback. The semiconductor memory which is provided to afford such a storage capacity is capable, in the device disclosed herein, of storing up to about 60-seconds of real-time information.

Compactness and portability characterize the proposed device, in that it can easily take the form, shape and size of a conventional hand-held dictation recorder.

These and other objects and advantages which are attained by the invention will become more fully apparent as the description which now follows is read in conjunction with the single drawing figure.

DESCRIPTION OF THE DRAWING

The single drawing figure is a block/schematic diagram of the apparatus of the invention shown connected to an external ECG machine.

DETAILED DESCRIPTION OF THE INVENTION

Turning to the single drawing figure, indicated generally at 10 is a portable two-way ECG data-storage device, or apparatus, constructed in accordance with the present invention. Device 10 is capable of operating, generally speaking, in both a capture/storage mode, and, selectively, in a retrieve/broadcast mode. Device 10 is intended to receive the information which it records by coupling to the usual two-conductor output terminals in a conventional external ECG machine, such as that shown at 12. In the drawing figure, device 10 and machine 12 are shown so connected through what is referred to herein in the device as an input/output interface structure, or port, 14.

Although it is not necessary that this be true, in device 10, port 14 is constructed in such a manner that it can alternately be coupled to the analogue output terminals of machine 12 or to the analogue input terminals, one at a time. In the schematic representation shown in the drawing, and for the sake of convenience, both connections are shown.

As will be more fully explained below, the device being disclosed herein is designed to be compact and portable, preferably having a configuration somewhat like that of a conventional hand-held dictation device, and to be capable of performing the flagged, time-windowed capture and recording of multiple-lead ECG data. In particular, device 10 is designed herein to be capable of receiving up to a full 12-lead packet of ECG data records.

Included, generally speaking, in the input/output interface structure are an amplifier/filter substructure 16, including an input unit 16a and an output unit 16b, and analogue/digital conversion means 18, including an input unit 18a and an output unit 18b.

This input/output interface structure, via connections with units 18a, 18b, is connected conventionally to a microprocessor and memory structure 20 which also forms part of the device.

Included in device 10, for audio outputting of information, is a voltage-controlled oscillator driver subunit 22 which is connected both to unit 18b, and to the microprocessor and memory structure, to supply, when so selected, audio information via a sound transducer 24.

User control of device 10 is provided by what is referred to herein as a user interface control means 26 which may take the form preferably of several push buttons accessible on the outside of the case housing the innerworkings of device 10.

Included in the microprocessor and memory substructure is a semiconductor memory which is capable of receiving and storing up to about 60-seconds, in real time, of digital data.

Considering how the device of the invention is put to use during the capture/storage mode, the unit is coupled, as is shown in the figure, to the analogue ECG output terminals of an external ECG machine, such as machine 12, is turned on, and then is instructed, seriatim, to engage in a time windowed recording cycle, herein of about 5-seconds. When the user of the equipment determines that an appropriate patient lead has been established, and that the analogue information made available at the machine's output terminals has stabilized, he or she actuates the control button which initiates recording. At this point in time, the microprocessor, because of the way in which it has been programmed, directs to the memory analogue-to-digital-converted data then arriving via units 16a, 18a. This activity is stopped automatically at the end of the selected time window, and an appropriate data flag is placed in the memory, again under microprocessor control, to identify what has just been recorded as one of the single records possibly storable in the memory.

To continue, the operator establishes another appropriate patient lead, waits until signal stabilization has occurred (as, for example, by looking at the activity on a strip chart recorder attached to the ECG machine) and again, through control 26, signals the microprocessor to establish another flagged, time-windowed reception of yet another lead of ECG, analogue-to-digital-converted data. This process then continues until all of the desired leads' ECG data has been received, up to a possible total herein of 12-leads.

Device 10 is so designed that, during the recording of data, and under instructions received at the microprocessor from control 26, a related audio signal may also be supplied via transducer 24, in real time, for local hearing and analysis, and/or for remote telephonic transmission.

When all the desired to-be-acquired data has in fact been acquired and stored, the device of the invention may be disconnected from the ECG machine, and carried conveniently anywhere for later retrieval, playback and/or broadcast of what has been recorded and stored. In the retrieve/broadcast mode, an operator, selectively, can output, via units 18b, 16b, digital-to-analogue-converted stored data to the analogue input terminals in a conventional ECG machine for whatever purposes are desired, as, for example, for creating a strip chart recording for study. The user may also select to operate the device in such a manner that an analogue artifact is created audibly which can be listened to via outputting through transducer 24 either in a manner tracking, in an analogue fashion the nature of the analogue data recorded originally, or, for example, in a frequency-keyed shifting manner for telephonic transmission.

Accordingly, and from the description which has just been given, it should be apparent that the device of the invention fills an important need, and addresses the issue suggested earlier herein. The subunits in device 10 illustrated in the drawing are, as individuals, constructible in any one of a variety of well known forms, and are easily incorporated in an effective, efficient and compact transportable unit which is envisioned by the invention.

While a preferred embodiment of the invention has thus been described, it is appreciated that variations and modifications may be made without departing from the spirit of the invention.

What is claimed is:

1. Portable, two-way ECG data-storage apparatus for the selective window-capturing, in the successive records, of plural-lead ECG data comprising
   a central digital processor and an associated semiconductor memory,
   an input/output interface structure selectively coupleable to the input and output analog terminals in an external ECG machine, said structure including analog/digital conversion means, operatively connected to said processor and memory for transferring ECG data to and from said memory,
   user-interface control means operatably connected to said processor, operable selectively, in a capture/storage mode, to effect, via processor operation, the capture and storage in said memory (for a limited preselected time window only) of converted analog ECG data arriving at said interface structure, and in a retrieve/broadcast mode to supply, for outputting via said interface structure, converted digital data then stored in said memory.

2. The apparatus of claim 1, wherein, when in the data capture/storage mode, said processor appropriately stores in said memory a flag associated with each of the individually time-windowed captured records of ECG data, said flag indicating the source of said associated individual ECG data.

3. The apparatus of claims 1 or 2 which further includes means operatively connected to said processor, operable thereby, with the apparatus in the retrieve/broadcast mode, to generate a selected pattern of audio sounds as an artifact representing information-characteristics of the data stored in said memory.

4. Portable, two-way ECG data-storage apparatus for the selective window-capturing, in the successive records, or plural lead ECG data comprising:
   a central digital processor and an associated semiconductor memory,
   an input/output interface structure selectively alternately coupleable to the input and output analog terminals in an external ECG machine one at a time, said structure including analog/digital conversion means, operatively connected to said processor and memory for transferring ECG data from such output analog terminal to said memory at a time when said structure is coupled thereto and from said memory to such input analog terminal at an alternate time when said structure is coupled thereto,
   user-interface control means operatably connected to said processor, operable selectively, in a capture/storage mode, to effect via processor operation, the capture and storage in said memory of converted analog ECG data arriving at said interface structure, and operable alternately, in a retrieve/broadcast mode to supply, for outputting via said interface structure, converted digital data then stored in said memory.

5. The apparatus of claim 4 which further includes means operatively connected to said processor, operable thereby, with the apparatus in the retrieve/broadcast mode, to generate a selected pattern of audio sounds as an artifact representing information-characteristics of the data stored in said memory.

* * * * *

UNITED STATES PATENT AND TRADEMARK OFFICE
CERTIFICATE OF CORRECTION

PATENT NO.   : 5,111,396
DATED        : May 5, 1992
INVENTOR(S)  : Gary N. Mills, Habib Homayoun & Herbert J. Semler It is certified that error appears in the above-identified patent and that said Letters Patent is hereby corrected as shown below:

Column 4:

In claim 4, line 3 change "or" to --of--; and change "plural lead" to --plural-lead--.

Signed and Sealed this

Sixth Day of July, 1993

Attest:

MICHAEL K. KIRK

*Attesting Officer*     Acting Commissioner of Patents and Trademarks